United States Patent [19]

Kaplan

[11] Patent Number: 5,916,543
[45] Date of Patent: Jun. 29, 1999

[54] EMULSIONS HAVING MINIMAL RUB-IN TIMES

[75] Inventor: Carl Kaplan, Memphis, Tenn.

[73] Assignee: Schering-Plough HealthCare Products, Inc., Memphis, Tenn.

[21] Appl. No.: 08/769,164

[22] Filed: Dec. 18, 1996

[51] Int. Cl.⁶ .............................. A61K 7/42; B01J 13/00
[52] U.S. Cl. ...................... 424/59; 424/401; 514/846; 514/941; 514/975; 516/73; 516/74; 516/76
[58] Field of Search ...................... 252/312, 314; 424/59, 401; 514/846, 941, 975; 516/74, 76, 73

[56] References Cited

U.S. PATENT DOCUMENTS

| | | | |
|---|---|---|---|
| 4,322,545 | 3/1982 | Scala, Jr. | 424/59 X |
| 4,675,179 | 6/1987 | Suzuki et al. | 514/941 X |
| 5,025,004 | 6/1991 | Wu et al. | 424/59 X |
| 5,229,104 | 7/1993 | Sottery et al. | 424/59 |
| 5,302,658 | 4/1994 | Gee et al. | 252/314 X |
| 5,599,528 | 2/1997 | Igaki | 424/59 |
| 5,674,509 | 10/1997 | Date et al. | 424/401 |
| 5,700,452 | 12/1997 | Deckner et al. | 424/59 |

FOREIGN PATENT DOCUMENTS

| | | | |
|---|---|---|---|
| 0579455 | 1/1994 | European Pat. Off. | A61K 7/00 |
| 19509079 | 9/1996 | Germany | A61K 7/00 |
| WO 93/11865 | 6/1993 | WIPO | B01F 17/00 |
| WO 94/02176 | 2/1994 | WIPO | A61K 47/32 |
| WO 94/23693 | 10/1994 | WIPO | A61K 7/42 |

OTHER PUBLICATIONS

C. Holden, "Formulating Hair and Skin Products More Effectively," *Specialty Chemicals*, vol. 16, pp. 21–23, 1996.

*Primary Examiner*—Richard D. Lovering
*Attorney, Agent, or Firm*—Robert A. Franks

[57] ABSTRACT

The invention encompasses oil-in-water type emulsion formulations having decreased skin rub-in times, comprising a nonaqueous phase, an aqueous phase and an oil-in-water emulsifier, which emulsion formulation also contains a water-in-oil emulsifier.

7 Claims, No Drawings

EMULSIONS HAVING MINIMAL RUB-IN TIMES

INTRODUCTION TO THE INVENTION

This invention relates to emulsion formulations for application to the skin, which emulsions have short rub-in time characteristics.

Numerous formulated materials are known for application to the skin; such as for cosmetic and/or therapeutic purposes. A large portion of these are emulsions, such as lotions or creams, which are composed of both aqueous and non-water soluble components.

In general, the sensations accompanying skin application of emulsions are more pleasant when oil-in-water, rather than water-in-oil, emulsions are used. Oil-in-water emulsions have nonaqueous material droplets completely surrounded or encapsulated by aqueous materials, so that the skin "feels" only aqueous materials upon application.

It is generally the case that a user will wish to not leave an applied emulsion on the skin surface after application, but will choose to rub the applied material for the purpose of causing its migration into the skin and concomitant "disappearance." With most uncolored compositions, it will not be possible to visually discern that anything has been applied to the skin, after the material has been rubbed in. It is very beneficial to the user to minimize the time required to rub an applied emulsion into the skin.

SUMMARY OF THE INVENTION

The invention encompasses an oil-in-water type emulsion formulation comprising a nonaqueous phase, an aqueous phase, and prepared using an oil-in-water emulsifier, which emulsion formulation also contains a water-in-oil emulsifier. The inventive formulations exhibit exceptionally short rub-in times on the skin and have a pleasing feel when applied. In addition, the emulsions can frequently be prepared by mixing ambient temperature (or heated only somewhat above ambient temperature) aqueous and nonaqueous phases, rather than the hot phase mixing required for typical skin care formulations.

DETAILED DESCRIPTION OF THE INVENTION

In this application, the term "percent" shall mean percent by weight, unless the context clearly indicates otherwise. Many of the formulation components are identified herein by their names as given in the monographs of J. A. Wenninger et al., *CTFA Cosmetic Ingredient Handbook, Second Edition*, The Cosmetic, Toiletry and Fragrance Association, Inc., Washington, D.C., 1992. This publication also identifies common uses of the ingredients.

The term "emulsion" shall be used herein to identify oil-in-water type dispersion formulations intended for application to the skin, particularly lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, emollients, humectants, ultraviolet radiation absorbers and the like, depending on the intended uses for the formulations. Also generally included in skin care products are formulation aids, such as film-forming polymers, emulsifiers, emulsion stabilizers, fragrances, thickeners, ionized substances, preservatives, antioxidants and the like.

Techniques for forming oil-in-water emulsions are very well known in the art. Typically, aqueous components are combined and mixed, nonaqueous components are combined and mixed, and then the two mixtures are combined under shear conditions to produce a stable emulsion. Emulsion formation typically depends upon the presence in one of the mixtures of a suitable surfactant "emulsifier"; emulsifiers for producing oil-in-water emulsions are of numerous chemical types, but are generally described as possessing HLB ("hydrophilic-lipophilic balance") values between about 8 and about 18. The HLB system has been used for a number of years by those skilled in this art to differentiate surfactants; see, for example U.S. Pat. No. 4,177,259 and references cited therein.

Numerous oil-in-water emulsifiers are known and can be used in the present invention. Representative examples of useful emulsifiers are sorbitan monolaurate, polyethylene glycol monolaurate, PEG 600 distearate, PEG 400 monooleate, glycerol monostearate, ethoxylated nonylphenol, polysorbate 20, 40 and 60, laureth-4 and -23, ceteth-2, -10 and -20, ceteareth-20, steareth-2, -10, -20, -21 and -100, oleth-2, -10 and -20, polyoxyethylene and polyoxypropylene ether of tridecyl alcohol (such as PPG-1-trideceth-6), polyethylene glycol octylphenol ether, polyoxyethylene sorbitan monostearate and sodium dodecyl diphenyloxide disulfonate. Mixtures of emulsifiers are frequently desirable for enhancing emulsion stability.

Certain commercial products combine emulsifiers with other desirable formulation components. Particularly useful for some emulsion products of the present invention are SALCARE™ SC91 and SALCARE™ SC96 which are available from Allied Colloids in Suffolk, Va., U.S.A. The SC91 product is a combination of the thickening and film-forming agent sodium polyacrylate copolymer, with mineral oil and the emulsifier PPG-1-trideceth-6. The SC96 product combines the thickening and film-forming agent polyquaternium 37 with the occlusive skin conditioner propylene glycol dicaprylate/dicaprate and the emulsifier PPG-1-trideceth-6. Both of these products facilitate ambient temperature or near-ambient temperature emulsification, particularly for formulations which do not contain supplemental oil-in-water emulsifiers. Heating is typically needed only to enhance the solubility of a component, where a solution is desired.

The present invention is based on a finding that the rub-in time of an oil-in-water emulsion can be markedly reduced by incorporating, in addition to the usual emulsifier therefor, an effective amount of a water-in-oil emulsifier. As is generally known, water-in-oil emulsifiers typically have HLB values in the range of about 1 to about 7. Numerous specific compounds are known to be useful for forming water-in-oil emulsions, a few representative examples being sorbitan monooleate, sorbitan sesquioleate, sorbitan trioleate, sorbitan monostearate, sorbitan isostearate, propylene glycol monostearate, PEG-22/dodecyl glycol copolymer, PEG-45/dodecyl glycol copolymer, PEG-22/dodecyl glycol copolymer, cetyl dimethicone copolyol, polyglyceryl-3-diisostearate, polyglyceryl-3 trioleate, polyglyceryl-4 oleate/PEG-8 propylene glycol cocoate, oleamide DEA, sodium glyceryl oleate phosphate and hydrogenated vegetable glycerides phosphate.

The water-in-oil emulsifier, which can comprise a mixture of individual emulsifying agents, will typically be present in the emulsion in amounts about 0.25 to about 5 percent. More preferably, amounts about 1 to about 3 percent will be used. For purposes of the present invention, preferred water-in-oil emulsifiers will generally have HLB values less than about 5.

The invention will be further illustrated by the following example, which is not intended to limit the scope of the invention, as defined by the appended claims, in any manner.

EXAMPLE

A series of cosmetic lotions, some containing dihydroxyacetone as an active ingredient for "sunless" tanning of the skin, are prepared using the ingredients listed in the following table. For each lotion, the rub-in time is determined and this value is also shown in the table.

| COMPONENT | I | II | III | IV |
|---|---|---|---|---|
| Water | 90.95 | 92.95 | 86.95 | 88.95 |
| Dihydroxyacetone | — | — | 4.00 | 4.00 |
| Propylene glycol isoceteth-3 acetate | 3.00 | 3.00 | 3.00 | 3.00 |
| Polyquaternium 37/propylene glycol dicaprylate dicaprate & PPG-1-trideceth-6 | 2.25 | 2.25 | 2.25 | 2.25 |
| Sorbitan isostearate | 2.00 | — | 2.00 | — |
| Glycereth-7 triacetate | 1.00 | 1.00 | 1.00 | 1.00 |
| Diazolidinyl urea | 0.30 | 0.30 | 0.30 | 0.30 |
| Fragrance | 0.25 | 0.25 | 0.25 | 0.25 |
| Vitamin E acetate | 0.10 | 0.10 | 0.10 | 0.10 |
| Aloe vera lipoquinone | 0.10 | 0.10 | 0.10 | 0.10 |
| Disodium EDTA | 0.05 | 0.05 | 0.05 | 0.05 |
| Time to rub in (seconds) | 20.3 | 39.8 | 22.9 | 43.1 |

The emulsions are prepared by: (1) combining the water, diazolidinyl urea, dihydroxyacetone and disodium EDTA to form a solution; (2) combining the remaining ingredients (except the SALCARE™ SC96, which contains 50% polyquaternium 37, 39% propylene glycol dicaprylate dicaprate and 7% PPG-1-trideceth-6) to form a uniform dispersion; (3) adding the step 1 mixture to the step 2 mixture, with agitation, to form a dispersion; and (4) adding the SALCARE™ SC96 to the step 3 dispersion to form the final emulsion. The water-in-oil emulsifier, sorbitan isostearate, is the commercial product CRILL™ 6 available from Croda, Inc. of New York, N.Y., U.S.A.

The rub-in test is performed by applying about 40 milligrams of emulsion inside an outlined 5 millimeters diameter circle on a subject's forearm, and then timing the moderate circular rubbing with a fingertip required until the subject detects an end to the initial "greasy" feeling in the circle. This test is rather subjective, and therefore comparing data between subjects cannot usually give meaningful results; however, it has been found that repetitive data from any single subject are surprisingly consistent.

The rub-in data in the table clearly indicate the surprising effect of including a low-HLB emulsifier in the emulsion. Rub-in times are decreased by approximately half when this ingredient is present.

What is claimed is:

1. An oil-in-water type emulsion formulation comprising: a nonaqueous phase; an aqueous phase containing dihydroxyacetone; an oil-in-water emulsifying agent comprising PPG-1-trideceth-6; Polyquaternium 37; and Propylene glycol dicaprylate dicaprate; and further containing 1 to about 3 weight percent of a water-in-oil emulsifying agent to decrease time required to rub the emulsion into skin.

2. The emulsion formulation of claim 1, wherein a water-in-oil emulsifying agent is at least one member selected from the group consisting of sorbitan monooleate, sorbitan sesquioleate, sorbitan trioleate, sorbitan monostearate, sorbitan isostearate, propylene glycol monostearate, PEG-22/dodecyl glycol copolymer, PEG-45/dodecyl glycol copolymer, PEG-22/dodecyl glycol copolymer, cetyl dimethicone copolyol, polyglyceryl-3-diisostearate, polyglyceryl-3 trioleate, polyglyceryl-4 oleate/PEG-8 propylene glycol cocoate, oleamide DEA, sodium glyceryl oleate phosphate and hydrogenated vegetable glycerides phosphate.

3. The emulsion formulation of claim 1, wherein the water-in-oil emulsifying agent comprises sorbitan isostearate.

4. An oil-in-water emulsion composition for sunless tanning, comprising water, dihydroxyacetone, polyquaternium 37, propylene glycol dicaprylate dicaprate, PPG-1-trideceth-6 and 1 to about 3 percent by weight of a water-in-oil emulsifying agent.

5. The composition of claim 4, wherein the water-in-oil emulsifying agent is at least one member selected from the group consisting of sorbitan monooleate, sorbitan sesquioleate, sorbitan trioleate, sorbitan monostearate, sorbitan isostearate, propylene glycol monostearate, PEG-22/dodecyl glycol copolymer, PEG-45/dodecyl glycol copolymer, PEG-22/dodecyl glycol copolymer, cetyl dimethicone copolyol, polyglyceryl-3-diisostearate, polyglyceryl-3 trioleate, polyglyceryl-4 oleate/PEG-8 propylene glycol cocoate, oleamide DEA, sodium glyceryl oleate phosphate and hydrogenated vegetable glycerides phosphate.

6. The composition of claim 4, wherein the water-in-oil emulsifying agent comprises sorbitan isostearate.

7. An oil-in-water emulsion composition for sunless tanning, comprising water, about 4 percent by weight dihydroxyacetone, about 2.25 percent by weight of a mixture of polyquaternium 37, propylene glycol dicaprylate dicaprate and PPG-1-trideceth-6, and about 2 percent by weight sorbitan isostearate.

* * * * *